United States Patent [19]
Back et al.

[11] Patent Number: 4,990,645

[45] Date of Patent: Feb. 5, 1991

[54] HYDROCYANATION PROCESS

[75] Inventors: Gary L. Back; Harvey J. Batey; John C. Caton, all of Victoria; Robin L. Kump, Orange; Charles F. O'Brien, III; Jacques D. Robinson, both of Victoria, all of Tex.

[73] Assignee: E. I. du Pont de Nemours and Company, Wilmington, Del.

[21] Appl. No.: 544,625

[22] Filed: Jun. 27, 1990

[51] Int. Cl.$^5$ ............................................. C07C 253/10
[52] U.S. Cl. ................................... 558/335; 558/435; 558/454
[58] Field of Search ............... 558/335, 338, 339, 340, 558/435, 454, 456

[56] References Cited

U.S. PATENT DOCUMENTS

| | | | |
|---|---|---|---|
| 3,752,839 | 8/1973 | Drinkard, Jr. et al. | 558/340 X |
| 3,920,721 | 11/1975 | Gosser | 558/339 |
| 4,080,374 | 3/1978 | Corn | 260/465.3 |
| 4,082,811 | 4/1978 | Shook, Jr. | 558/335 X |
| 4,382,038 | 5/1983 | McGill | 558/338 |
| 4,416,824 | 11/1983 | Reimer et al. | 558/435 X |
| 4,810,815 | 3/1989 | Bryndza | 558/335 X |

*Primary Examiner*—Joseph Paul Brust

[57] ABSTRACT

An improved process for the hydrocyanation of pentenenitrile which comprises adding solid catalyst degradation precipitate to the hydrocyanation reactor, and operating the reactor at a level of HCN concentration such that the product fluid leaving the reactor has an HCN concentration of less than about 2500 parts per million parts of fluid.

6 Claims, 1 Drawing Sheet

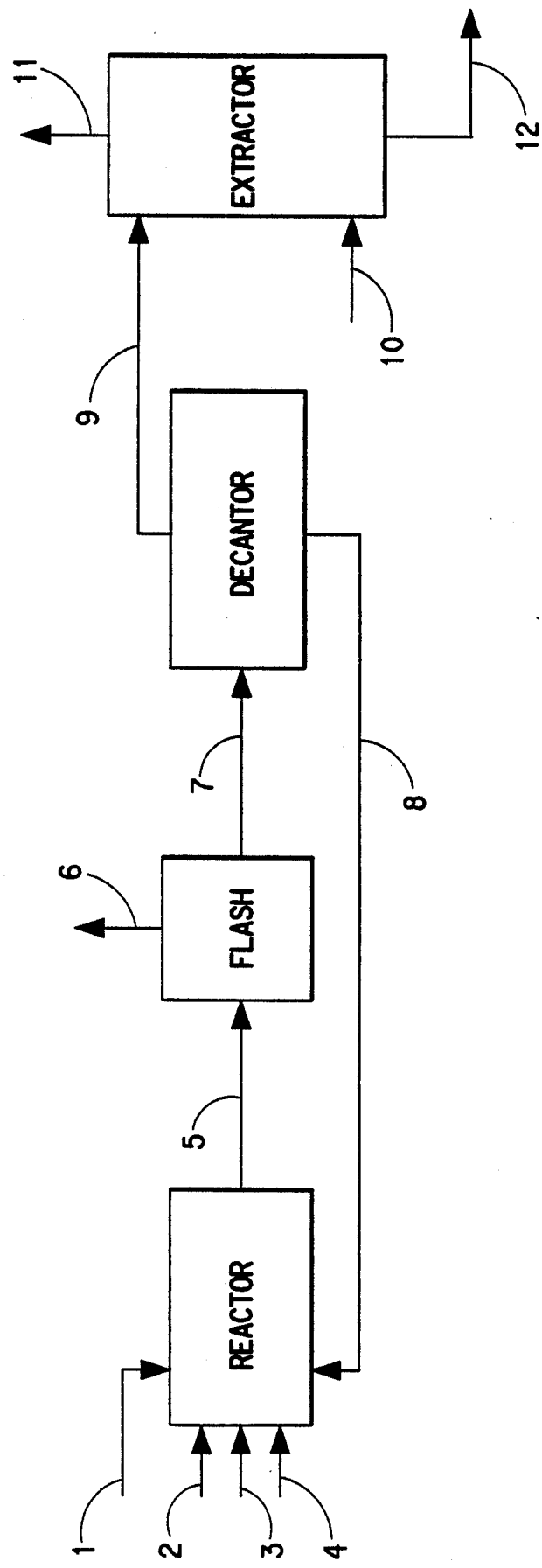

HYDROCYANATION PROCESS

FIELD OF THE INVENTION

This invention relates to the process of preparation of adiponitrile by the hydrocyanation of pentenenitrile using a zero-valent nickel catalyst and a triarylborane promoter. More particularly this invention relates to running this process in a more efficient manner by reducing the amount of solid catalyst degradation precipitate that encrusts on equipment surfaces to cause operability problems. Also, this invention allows the removal of the solid catalyst degradation precipitate from the product fluid before all the zero-valent nickel compound (catalyst) is recovered from the product stream, and allows the efficient separation of catalyst from the product fluid. The solid catalyst degradation precipitate comprises $Ni[NC(CH_2)_4CN]_2[NCB\phi_3]_2$, hereinafter sometimes referred to as NCBC.

BACKGROUND OF THE INVENTION

U.S. Pat. No. 4,080,374 to Corn discloses that during hydrocyanation of pentenenitrile to adiponitrile some zero-valent nickel catalyst is oxidized to nickel cyanide which forms insoluble complexes with triarylborane. These insoluble complexes (solid catalyst degradation precipitate) become encrusted on the equipment surfaces, and lead to inefficient operation by loss of heat transfer capability and restriction of flow through the equipment. Some of the solid catalyst degradation precipitate remains suspended in the product fluid and interferes with efficient recovery of the zero-valent nickel catalyst by liquid/liquid extraction from the product fluid.

SUMMARY OF THE INVENTION

The present invention is an improvement in the process for the preparation of adiponitrile by the hydrocyanation of pentenenitrile using a zero-valent nickel catalyst and a triarylborane promoter in which solid catalyst residue forms a precipitate which fouls the reactor and related equipment, and is also contained in the product stream at a high enough concentration that makes separation of the zero-valent nickel catalyst from the product fluid difficult. The improvement comprises removing a portion of the precipitate from the product stream, and recycling at least a portion of the removed precipitate to the reactor.

The addition of the precipitate to the reactor apparently provides a substitute surface on which newly forming catalyst degradation product can precipitate, thereby resulting in a reduction in the amount of catalyst degradation product that becomes encrusted on the surface of the reactor and related equipment. Furthermore, the solid catalyst degradation precipitate contained in the product stream after the deliberate addition of catalyst degradation precipitate is more easily separated from the product fluid, and as a consequence does not interfere with the separation of zero-valent catalyst from the product fluid. The catalyst degradation product that forms the precipitate contains a high proportion of NCBC.

In the usual practice of the process of this invention the reactor will contain a mixture of pentenenitrile, hydrogen cyanide, triarylborane, zero-valent nickel catalyst (fresh catalyst as well as recycled catalyst) and added solid catalyst degradation precipitate. The amounts and proportions of the ingredients, other than added solid catalyst degradation precipitate are conventional and are described in the prior art and well-known to one skilled in the art. The hydrogen cyanide concentration normally will be less than 2500 ppm, preferably less than 1000 ppm, of the reactor fluid. At levels of about 500 ppm the hydrogen cyanide concentration is normally sufficient to react efficiently with the pentenenitrile, but is insufficient to cause the zero-valent nickel catalyst to form unduly large amounts of precipitate—i.e. solid catalyst degradation precipitate. The amount of this solid added to the reactor can vary widely but is usually in the range of about 0.3 wt.% to about 2.5 wt.% of the reactor fluid, preferably about 1 to about 1.5 wt.%.

DESCRIPTION OF THE DRAWING

The drawing is a schematic of the hydrocyanation process which depicts the process of the invention.

DETAILED DESCRIPTION OF THE INVENTION

The feed material for the process of the invention is pentenenitrile. If the nitrile is 3-pentenenitrile it isomerizes in situ to 4-pentenenitrile. The 4-pentenenitrile is converted to adiponitrile by the addition of one molecule of hydrogen cyanide. With reference to the drawing, stream 1 of pentenenitrile is fed to the reactor along with stream 2 of HCN, stream 3 of triarylborane, and stream 4 of zero-valent nickel catalyst. Stream 8 is a recycle stream containing zero-valent nickel catalyst and solid catalyst degradation precipitate. In the practice of this invention it is necessary to recycle solid catalyst degradation precipitate and to maintain reaction conditions such that concentration of HCN in the product stream leaving the reactor does not exceed about 2500 ppm. At higher concentrations of HCN, the solid catalyst degradation precipitate apparently becomes charged and is prone to remain associated with the polar adiponitrile molecules rather than separate with catalyst in the decanter. After reaction the product fluid is passed via stream 5 to the flasher where unreacted pentenenitrile is removed as stream 6. (This stream 6 will normally be recycled to the reactor). The crude adiponitrile passes by stream 7 to the decanter where two phases form. Operating temperatures of 45° C. or less have been found to improve separation of active as well as solid catalyst degradation precipitate from the mixture in the decanter. The upper phase contains most of the adiponitrile and the lower phase, most of the zero-valent nickel catalyst. By employing the carefully selected process operating conditions described herein and by recycling a fraction of degradation precipitate to the reactors, it is possible to cause substantially all of the solid catalyst degradation precipitate to settle with the catalyst phase in the decanter. The lower phase is separated as stream 8, and the upper phase separated as stream 9. U.S. Pat. No. 4,539,302 to Leyendeker et al describes in considerable detail process conditions suitable to carry out the steps of reaction, flashing and decantation. The upper phase is passed by stream 9 to the extractor where additional active catalyst is recovered along with excess ligand. U.S. Pat. No. 3,773,809 describes in considerable detail the operation of the extractor. The extracting organic solvent is fed as stream 10 to the extractor, and the purified stream of adiponitrile forms stream 12. The extracted ligand and catalyst contained in stream 11, is then used to prepare additional catalyst for feed to the reactor.

The amount of solid catalyst degeneration precipitate in the system will increase to an unsatisfactory level unless measures are taken to eliminate a portion of this solid. The amount of solid catalyst residue that is present in the system is controlled by periodically or continuously treating all or a portion of stream 8 with a pentenenitrile wash whereby the catalyst (zero-valent nickel compound) is dissolved in the pentenenitrile, and the excess solid catalyst degradation precipitate is discarded. The pentenenitrile containing the dissolved catalyst and the desired amount of solid catalyst degradation precipitate is then recycled to the reactor. The liquid/liquid extraction of zero-valent nickel compound can be used to remove almost all of the solid catalyst degradation precipitate from the recycled catalyst stream if this result is desired.

The fouling of the process equipment is significantly reduced by the addition of solid catalyst degradation precipitate to the reactor, and if the HCN concentration in the reactor is properly controlled so that the HCN concentration in the product stream is less than about 2500 ppm, solid catalyst degradation precipitate is more easily removed from the product fluid in the decanter. This may be due to larger particle size, more uniform particle size distribution, higher density of the particles, a combination of the above factors, or because of one or more of these factors and one or more unknown factors.

EXAMPLES

EXAMPLE NO. 1, REDUCED FLASHER FOULING

A pentenenitrile hydrocyanation unit configured approximately as described in the attached drawing was operated without solids recycle. Feeds entering the flasher stream 5 contained 0.07 wt.% solid catalyst degradation precipitate, largely NCBC. The flasher tails, stream 7, had 0.14 wt.% solids. The flash unit operated 29 days before becoming so fouled with this encrusted solid that it was necessary to shut down and remove the deposits. During this 29 day period it was necessary to swap and clean the flasher calandrias seven times.

A second run on the unit was made under approximately the same operating conditions except the solid catalyst degradation precipitate concentration of reactor product (stream 5) was controlled to 1.4% by adding solid NCBC to the reactor feed. Solids content of the flasher tails, stream 7, rose to 2.0% and the fouling rate of process equipment was greatly reduced. The system operated 95 days before it was necessary to shut down for cleaning. During this period, the flasher calandrias were cleaned only five times.

EXAMPLE NO. 2, DECANTER SOLIDS RECOVERY

The pentenenitrile unit described in Example No. 1 was operating at steady state conditions with 99% recovery of solid catalyst degradation precipitate entering the decanter being recovered in stream 8 and only 1% leaving the decanter in stream 9. The HCN concentration of the reactor product (stream 5) was increased from 500 ppm to 3000 ppm. The $Ni(CN)_2$ concentration in system solids increased from 3.5 to 7.7 wt.%. Soon after the affected product reached the decanter, the preponderance of solid catalyst degradation precipitate entering the decanter began exiting the decanter in stream 9. The solid catalyst degradation precipitate formed an emulsion that caused the extractor to flood. The HCN concentration was returned to 0.05 wt.%. Soon thereafter, solid catalyst degradation precipitate exiting the decanter in stream 9 returned to its former 1% level and concentration of the solid catalyst degradation precipitate in stream 8 began building. Extractor flooding ceased.

We claim:

1. A process for the preparation of adiponitrile by the hydrocyanation of pentenenitrile using a zero-valent nickel catalyst and a triarylborane promoter in which solid catalyst degradation precipitate fouls the reactor and related equipment and is contained in the product fluid which comprises recycling a portion of the solid catalyst degradation precipitate to the reactor, and controlling the HCN concentration in the product stream leaving the reactor so that the HCN concentration does not exceed about 2500 ppm.

2. The process of claim 1 in which the amount of solid catalyst degradation precipitate recycled is controlled by removing a portion of the solid catalyst degradation product precipitate that is contained in a stream of zero-valent nickel compound that is being recycled to the reactor.

3. The process of claim 2 in which the portion of the solid catalyst degradation precipitate that is removed from the stream of zero-valent nickel compound is removed by washing said stream with pentenenitrile and the wash solution fed to the reactor.

4. The process of claim 1 in which the precipitate contains NCBC.

5. The process of claim 1 in which pentenenitrile is removed from the product fluid before the precipitate is removed from the product fluid.

6. The process of claim 1 in which the amount of precipitate that is fed to the reactor is in the range of about 0.3 wt.% to about 2.5 wt.% of the total weight of the components in the reactor.

* * * * *